US012330155B2

(12) United States Patent
Kang et al.

(10) Patent No.: US 12,330,155 B2
(45) Date of Patent: Jun. 17, 2025

(54) METHOD FOR ISOLATING EXTRACELLULAR VESICLES

(71) Applicant: KOREA INSTITUTE OF SCIENCE AND TECHNOLOGY, Seoul (KR)

(72) Inventors: Ji Yoon Kang, Seoul (KR); Bo Hoon Han, Seoul (KR); You Hee Heo, Seoul (KR); Kyeong Sik Shin, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 995 days.

(21) Appl. No.: 16/682,865

(22) Filed: Nov. 13, 2019

(65) Prior Publication Data
US 2020/0188918 A1 Jun. 18, 2020

(30) Foreign Application Priority Data

Dec. 18, 2018 (KR) .......... 10-2018-0164590

(51) Int. Cl.
G01N 1/34 (2006.01)
B01L 3/00 (2006.01)

(52) U.S. Cl.
CPC .......... B01L 3/502761 (2013.01); G01N 1/34 (2013.01); B01L 2200/0668 (2013.01); B01L 2300/0861 (2013.01)

(58) Field of Classification Search
CPC .......... B01L 3/502761; B01L 2200/064; G01N 1/34
See application file for complete search history.

(56) References Cited

U.S. PATENT DOCUMENTS

| | | | | |
|---|---|---|---|---|
| 10,590,371 B1 * | 3/2020 | Huang | ...... | C12M 1/02 |
| 10,590,372 B2 * | 3/2020 | Park | ...... | C12Q 1/24 |
| 11,016,009 B2 * | 5/2021 | Park | ...... | C12Q 1/6806 |
| 2018/0164197 A1 * | 6/2018 | Park | ...... | C12Q 1/24 |
| 2020/0188918 A1 * | 6/2020 | Kang | ...... | G01N 1/34 |

OTHER PUBLICATIONS

Chen et al., 2010. Microfluidic isolation and transcriptome analysis of serum microvesicles. Lab on a Chip, 10(4), pp. 505-511. (Year: 2010).*
Chiriaco et al., 2018. Lab-on-chip for exosomes and microvesicles detection and characterization. Sensors, 18(10), 3175 pp. 1-41. (Year: 2018).*
Davies et al., 2012. Microfluidic filtration system to isolate extracellular vesicles from blood. Lab on a Chip, 12(24), pp. 5202-5210. (Year: 2012).*
Dudani et al., 2015. Rapid inertial solution exchange for enrichment and flow cytometric detection of microvesicles. Biomicrofluidics, 9(1), 014112 pp. 1-10. (Year: 2015).*
Iqbal et al., 2016. Aqueous two-phase system (ATPS): an overview and advances in its applications. Biological procedures online, 18(1), pp. 1-18. (Year: 2016).*
Han et al., 2020. Isolation of extracellular vesicles from small volumes of plasma using a microfluidic aqueous two-phase system. Lab on a Chip, 20(19), pp. 3552-3559. (Year: 2020).*
Hardt., 2012. Microfluidics with aqueous two-phase systems. Lab on a Chip, 12(3), pp. 434-442. (Year: 2012).*
Kang et al., 2017. Methods to isolate extracellular vesicles for diagnosis. Micro and Nano Systems Letters, 5(1), pp. 1-11. (Year: 2017).*
Krbas et al., 2019. Optimized isolation of extracellular vesicles from various organic sources using aqueous two-phase system. Scientific reports, 9(1), pp. 1-11. (Year: 2019).*
Kordelas et al., 2014. MSC-derived exosomes: a novel tool to treat therapy-refractory graft-versus-host disease. Leukemia, 28(4), pp. 970-973. (Year: 2014).*
Liga et al., 2015. Exosome isolation: a microfluidic road-map. Lab on a Chip, 15(11), pp. 2388-2394. (Year: 2015).*
Liu et al., 2017. Field-free isolation of exosomes from extracellular vesicles by microfluidic viscoelastic flows. ACS nano, 11(7), pp. 6968-6976. (Year: 2017).*
Santana et al., 2014. Microfluidic isolation of cancer-cell-derived microvesicles from hetergeneous extracellular shed vesicle populations. Biomedical microdevices, 16(6), pp. 869-877. (Year: 2014).*
Shin et al., 2015. High-yield isolation of extracellular vesicles using aqueous two-phase system. Scientific reports, 5(1), pp. 1-11. (Year: 2015).*
Shin et al., 2018. Aqueous two-phase system to isolate extracellular vesicles from urine for prostate cancer diagnosis. PLoS One, 13(3) e0194818 pp. 1-15. (Year: 2018).*
SooHoo, J.R. and Walker, G.M., 2009. Microfluidic aqueous two phase system for leukocyte concentration from whole blood. Biomedical microdevices, 11(2), pp. 323-329. (Year: 2009).*
Smith et al., 2018. Integrated nanoscale deterministic lateral displacement arrays for separation of extracellular vesicles from clinically-relevant volumes of biological samples. Lab on a Chip, 18(24), pp. 3913-3925. (Year: 2018).*
Weng et al., 2016. Effective isolation of exosomes with polyethylene glycol from cell culture supernatant for in-depth proteome profiling. Analyst, 141(15), pp. 4640-4646. (Year: 2016).*
Yang et al., 2017. Exosome separation using microfluidic systems: Size-based, immunoaffinity-based and dynamic methodologies. Biotechnology Journal, 12(4), 1600699 pp. 1-8. (Year: 2017).*
Gholizadeh et al., 2017. Microfluidic approaches for isolation, detection, and characterization of extracellular vesicles: current status and future directions. Biosensors and Bioelectronics, 91, pp. 588-605 (Year: 2017).*
Han et al., Taiwan Kaohsiung, 22nd International Conference on Miniaturized Systems for Chemistry and Life Sciences, Nov. 11-15, 2018, M195g, pp. 157-159, total 159 pages.

(Continued)

Primary Examiner — Gary Benzion
Assistant Examiner — Olayinka A Oyeyemi
(74) Attorney, Agent, or Firm — Birch, Stewart, Kolasch & Birch, LLP

(57) ABSTRACT

The present invention relates to a method for isolating extracellular vesicles comprising: preparing a microfluidic chip in which at least two microfluidic channels are formed and inlets and outlets are formed at both ends of the channels, respectively; injecting at least one aqueous solution into the inlet of the microfluidic chip to form a microfluid; injecting a sample containing extracellular vesicles into the inlet of the microfluidic chip; and recovering the fluid from the outlet of the microfluidic chip.

5 Claims, 5 Drawing Sheets

(56) References Cited

OTHER PUBLICATIONS

Hardt, S. and T. Hahn, "Microfluidics with aqueous two-phase systems," Lab Chip (2012), vol. 12, pp. 434-442.
Liu et al., "Field-Free Isolation of Exosomes from Extracellular Vesicles by Microfluidic Viscoelastic Flows," ACS Nano (2017), vol. 11, pp. 6968-6976.
Soohoo, J. R. and G. M. Walker, "Microfluidic aqueous two phase system for leukocyte concentration from whole blood," Biomed Microdevices (2009), vol. 11, pp. 323-329.
Tsukamoto et al., "Cell separation by an aqueous two-phase system in a microfluidic device," Analyst (2009), vol. 134, pp. 1994-1998.

* cited by examiner

EVs collected from middle outlet

N=143
Height mean: 36.336 nm

METHOD FOR ISOLATING EXTRACELLULAR VESICLES

CROSS-REFERENCES TO RELATED APPLICATIONS

This application claims the benefit of and priority to Korean Patent Application No. 2018-0164590, filed on Dec. 18, 2018, which is incorporated herein by this reference in its entirety.

TECHNICAL FIELD

The present invention relates to a method for isolating extracellular vesicles, and more particularly, to a method for isolating extracellular vesicles using microfluidics.

BACKGROUND ARTS

Extracellular vesicles refer to a heterogeneous set of nanoscale vesicles surrounded by membranes carrying complex baggage including proteins, lipids and nucleic acids. Extracellular vesicles are divided into tens of nanometers of exosomes and hundreds of nanometers of microvesicles, which were previously known to be a mere means for eliminating unnecessary nonfunctional cellular components. However, they are known to have the role of mutual information exchange between cells, as well as the functions with respect to tumor metastasis, immune response, and tissue regeneration, etc. has been reported, and also known as a biomarker associated with the diagnosis of certain diseases, such as cancer. Generally, endosomes including intraluminal membrane vesicles (IMVs), are maturated intracellularly into multivesicular bodies containing a number of IMVs and the maturated multivesicular bodies are released from the cell by fusing with plasma membrane, and eventually exosomes are generated by the procedure. Microvesicles are known to be produced through the budding of the cell membrane, unlike the exosomes (FIG. 1).

In addition, in recent years, since they are vesicles surrounded by living cell membranes, their use as drug carriers for carrying drugs therein or on the surfaces thereof has also been highlighted.

Because of the wide availability of these extracellular vesicles, there is an absolute need for a technology for efficiently isolating them from cell culture media and body fluids.

Methods for isolating extracellular vesicles include ultracentrifugation (Momen-Heravi et al., *Mothods Mol. Biol.* 1660:25-32, 2017), size exclusion chromatography (Gamez-Valero et al., *Sci. Rep.* 6: 33641, 2016), and polymer precipitation (Niu et al., *PLoS ONE,* 0186534, 2017) were reported. However, the above-mentioned methods require large volumes of samples and expensive equipment, or they are labor- or time-consuming. In order to solve the problems of the methods, a method for isolating microfluidic channel-based extracellular vesicles using antibodies has been proposed (Guo et al., *J. Extracell. Vesicles,* 7 (1): 1508271, 2018). Since different surface markers are expressed for each, separation using only one antibody specific to these markers is not only highly likely to be lost for the vesicles that do not express the marker, but also has a disadvantage of high cost because the antibody is used.

On the other hand, aqueous two-phase systems (ATPS) referred as to a layer separation system in which two or more polymers or a polymer and a salt are both dispersed or dissolved in water, but are not mixed with each other when dispersing or dissolving in water due to their poor compatibilities with each other. Examples thereof include polyethylene glycol/dextran aqueous two-phase systems, polyethylene glycol/potassium phosphate aqueous two-phase systems, and the like. Recently, a method for separating extracellular vesicles using the aqueous two-phase system has been reported (Kim et al., *PLoS ONE,* 10 (6): e0129760, 2015; Shin et al., *PLoS ONE,* 13 (3)). e0194818, 2018). However, these methods are cumbersome because they require lots of labor and are not suitable for smaller samples because it requires a sample amount of at least 200 µl or more.

Therefore, the development of more efficient microfluidic channel-based method for isolating extracellular vesicles is required.

DISCLOSURE OF THE INVENTION

Technical Problem

The present invention is to solve various problems, including the disadvantages of the prior arts as described above, it is an object of the present invention to provide a more efficient microfluidic channel-based method for isolating extracellular vesicles. However, these problems are exemplary, and the scope of the present invention is not limited thereby.

SUMMARY OF THE INVENTION

In an aspect of the present invention, a method for isolating extracellular vesicles comprising: preparing a microfluidic chip in which at least two inlets and outlets are formed at both ends of the channels, respectively; injecting at least one aqueous solution into the inlet of the microfluidic chip to form multi-phase microfluid; injecting a sample containing extracellular vesicles into the inlet of the microfluidic chip; and recovering the fluid from the outlet of the microfluidic chip.

Effect of the Invention

According to one embodiment of the present invention made as described above, it is possible to isolate the extracellular vesicles with a very high yield as well as purity while using a small volume of the sample. Of course, the scope of the present invention is not limited by these effects.

DETAILED DESCRIPTION OF THE INVENTION

Definitions

Figure 1:
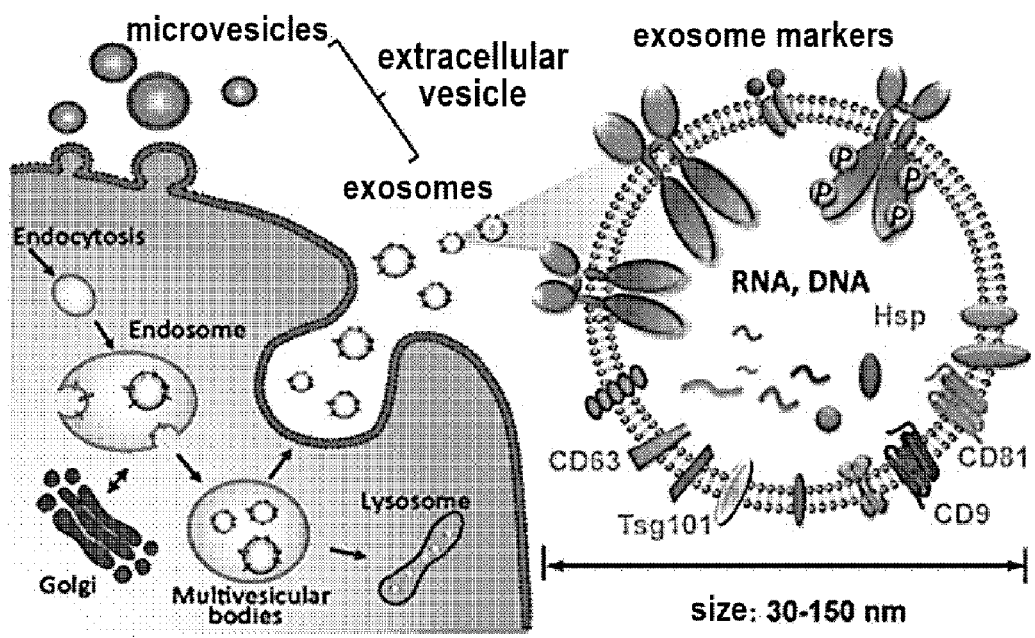
FIG. 1 is a schematic diagram showing a biogenesis and release of microvesicles and exosomes from cells.

As used herein, the term "extracellular vesicle" refers to a heterogeneous collection of nanoscale small vesicles surrounded by membranes containing complex baggage containing proteins, lipids, and nucleic acids. The extracellular vesicle includes an exosome and a microvesicle.

As used herein, the term "exosome" refers to a small size (30-150 nm) nanovesicle which is secreted from cells containing sophisticated RNAs and proteins and it is understood that it specifically secreted for intercellular signal transduction.

As used herein, the term "microvesicle" refers to a small size vesicle generally larger (100 to 1,000 nm) than exosomes, generated through budding from cells, and it is found in interstitial space between cells or various body fluids.

As used herein, the term "aqueous two-phase system" (ATPS) refers to a layer separation system in which two or more polymers or a polymer and a salt are both dispersed or dissolved in water, but are not mixed with each other when dispersing or dissolving in water due to their poor compatibilities with each other.

DETAILED DESCRIPTION OF THE INVENTION

In an aspect of the present invention, a method for isolating extracellular vesicles comprising: preparing a microfluidic chip in which at least two microfluidic channels are formed and inlets and outlets are formed at both ends of the channels, respectively; injecting at least one aqueous solution into the inlet of the microfluidic chip to form a multi-phase microfluid; injecting a sample containing extracellular vesicles into the inlet of the microfluidic chip; and recovering the fluid from the outlet of the microfluidic chip.

According to the method, the aqueous single-phase microfluid may be formed by a single aqueous solution but have different flow rates according to channels, or an aqueous phase two-phase microfluid formed by a first aqueous solution and a second aqueous solution which are not mixed with each other. The first aqueous solution may be water or a aqueous solution in which at least one first solute selected from the group consisting of water, or polyethylene glycol, polyvinylpyrrolidone, polyvinyl alcohol, and picol is dissolved in water, and the second aqueous solution may be an aqueous solution in which at least one second solute selected from the group consisting of EOPO (ethylene oxide propylene oxide), dextran, high concentration salt, levan, poly (vinyl methyl ethyl ether), ammonium sulfate, sodium sulfate, magnesium sulfate, potassium phosphate and sodium carbonate is dissolved in water.

According to the method, the microfluidic channel may be composed of three channels of an upper channel, an intermediate channel, and a lower channel, or two channels of a central channel and an outer channel of a concentric circle surrounding the central channel (Korean Patent No. 1061544). In the former case, the first aqueous solution may be injected into the upper channel and the lower channel, and the second aqueous solution may be injected into the intermediate channel. In the latter case, the second aqueous solution may be injected into the central channel, and the first aqueous solution may be injected into the outer channel. When a single phase is used, the aqueous solution is injected simultaneously into all channels, but the sample containing the extracellular vesicles may be selectively injected only into the intermediate channel or the central channel.

According to the method, the concentration of the first solute may be 1 to 5 wt %.

According to the method, the concentration of the second solute may be 1 to 2 wt %.

According to the method, the difference in flow rate of the single aqueous solution may be 0.5 to 3 µl/min.

According to the method, the flow rate of the first aqueous solution may be 1 to 5 µl/min.

According to the method, the flow rate of the second aqueous solution may be 0.5 to 3.5 µl/min.

According to the method, the sample may be cell culture media, sweat, tear, urine, serum, or plasma.

According to the method, the extracellular vesicles may be exosomes or microvesicles.

Hereinafter, the present invention would be described in more detail by the following examples. It should be understood, however, that the invention is not limited to the examples, but may be embodied in many different forms and should not be construed as limited to the examples set forth herein. Rather, these examples are provided so that this disclosure will be thorough and complete, and it is provided to fully inform a skilled in the art the scope of the present invention.

EXAMPLES

Example 1: Preparation of Three-Channel Microfluidic Chips

Figure 2:
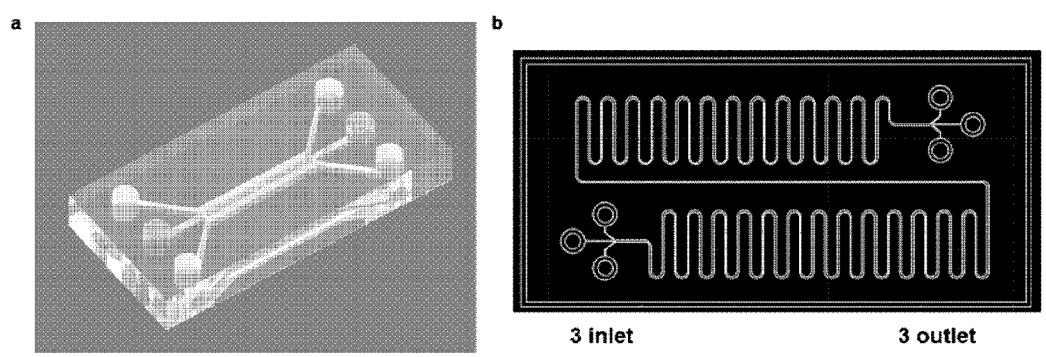
FIG. 2 is a schematic diagram representing a three-channel microfluidic chip according to an embodiment of the present invention, a) a schematic diagram showing the design of a three-channel microfluidic chip of the present invention, b) an actual microfluidic chip manufactured by the example 1 of the present invention.

The present inventors prepared a three-channel microfluidic chip with three inlets and three outlets for the isolation of extracellular vesicles (FIG. 2b). Specifically, the width of each channel was set to 50 µm, the depth of the channel was set to 100 µm, and the length of the channel was set to 36.7 cm. An injection pump is coupled to the inlet of the injection part of each channel.

Example 2: Fabrication of Concentric Two-Channel Microfluidic Chips

The inventors have produced a concentric, two-channel microfluidic chip with an inlet and an outlet for isolating extracellular vesicle according to the method described in Korean Patent No. 1051544.

Experimental Example 1: Exosome Isolation Using Exosome-Protein Mixture

The present inventors first performed an exosome separation experiment using a mixed solution of exosomes and protein bovine serum albumin (BSA) to determine whether the microfluidic chip of the present invention can be used for the isolation of extracellular vesicles.

Figure 3:
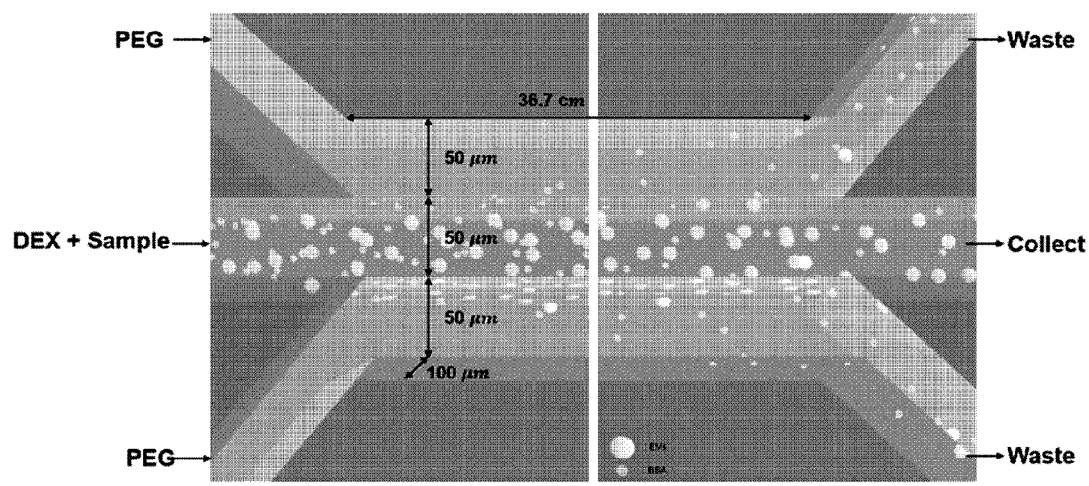
FIG. 3 is a schematic diagram showing the principle of separation of extracellular vesicles using a three-channel aqueous two-phase microfluidic chip according to an embodiment of the present invention.
Figure 6:
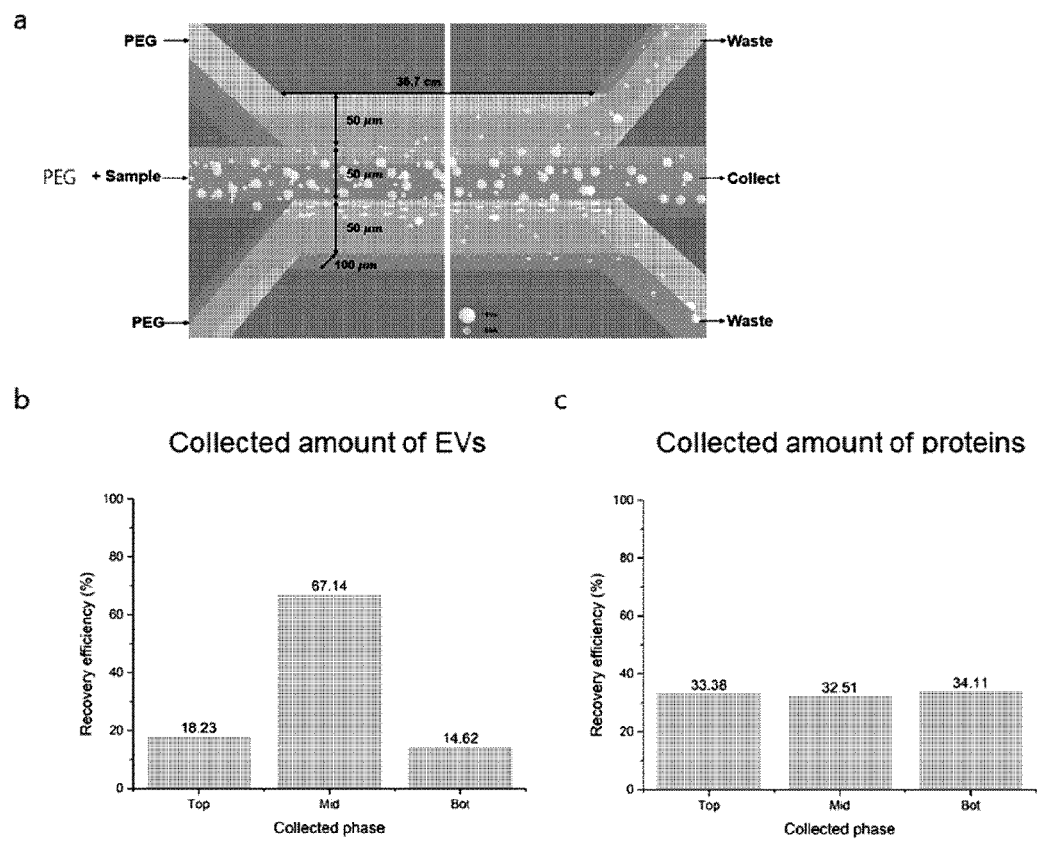
FIG. 6 is a schematic diagram showing the isolation process of extracellular vesicles using a three-channel single-phase microfluidic chip as a control (a) and a series of graphs showing the recovery of collected exosomes (b) and BSA (c) in each phase.

Specifically, in the upper and lower phases of the 3-channel microfluidic chip, a solution in which 3.5 wt % polyethylene glycol (PEG, average molecular weight 30 kDa) was dissolved in PBS was used as a fluid. In the middle phase, a solution in which 1.5 wt % dextran (DEX, average molecular weight 500 kDa) was dissolved in PBS was used (FIG. 3), and the flow rate was set to 3 μl/min for PEG solution, and the flow rate for DEX solution was set to 2 μl/min. As a control, a single phase system using PEG in all three phases was used (FIG. 6a). In this case, sample solution was injected in the middle channel and flow rates were set as above (upper and lower channel: 3 μl/min and middle channel: 2 μl/min).

Figure 4:
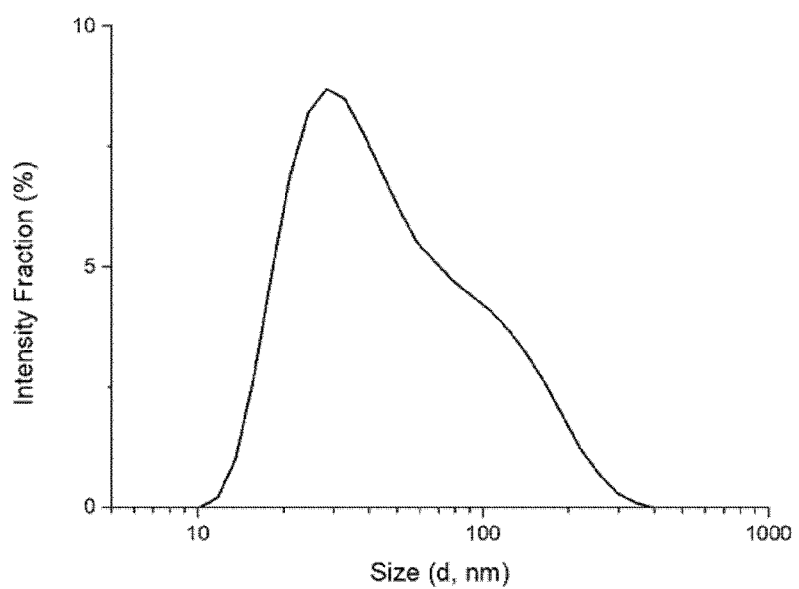
FIG. 4 is a histogram showing the results of analyzing the size distribution of exosomes labeled with PKH67 by light scattering analysis (DLS).

Then, exosomes were labeled with PKH67 Cell Linker (Sigma-Aldrich, USA) in order to label the exosomes fluorescently, and bovine serum albumin labeled with Alexa 594 phosphor was purchased from Thermo Fischer Scientific, Inc. (FIG. 4). The diameter distribution of labeled exosomes after PKH67 labeling was examined by dynamic light scattering (DLS) analysis. As shown in FIG. 4, the size distribution of the labeled exosomes was similar to that of the exosomes widely known.

Figure 5:
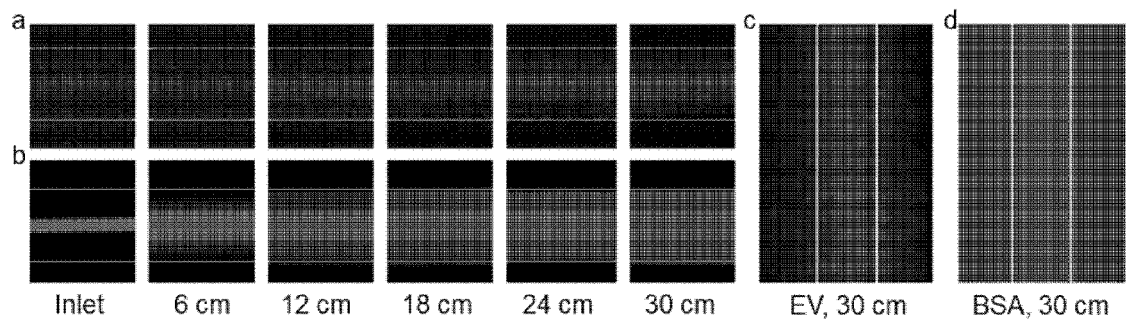
FIG. 5 shows a result of visualizing the fluorescence by exosomes (a) and BSA (b) at each distance of fluid flow using a three-channel aqueous two-phase microfluidic chip according to an embodiment of the present invention and magnified images (c and d) at 30 cm of distance of a and b, respectively.

After mixing the exosomes labeled with PKH67 and BSA labeled with Alex 594 as described above, 400 μl of the mixed solution was loaded in the inlet of the intermediate phase, and the fluids flowed in three channels at the above-described flow rates. At this time, the concentration of loaded exosomes was set to $2.41 \times 10^{11}$ particles/ml, and the concentration of loaded BSA was set to 631.3 μg/ml. Fluorescence was measured to determine the fraction of exosomes and BSA while the fluid was flowing (FIG. 5). As a result, as shown in FIG. 5a, the most of exosomes were found in the intermediate phase due to minimized diffusion of exosomes even though the fluid flow is increased. On the contrary, it was confirmed that BSA initially stayed in the middle phase, but diffused into the upper and lower phases over time, as shown in FIG. 5.

To verify the reliability of the fluorescence assay, the concentrations of exosomes and BSA were measured directly in the sample collected through the outlet. Specifically, the concentration of exosomes was measured by nanoparticle tracking analysis (NTA) (Dragovic et al., *Nanomedicine* 7(6): 780-788, 2011), and the concentration of BSA was analyzed by Bradford assay.

As a result, as shown in FIG. 6a, 67.14% of exosomes were collected and 67.49% of BSAs of the control group were removed even though single phase was used. The efficacy of 67.14% identified in the single phase isolation is a very high yield compared to the conventional isolation method, showing that the separation using the microfluidic channel of the present invention is very efficient.

Figure 7:
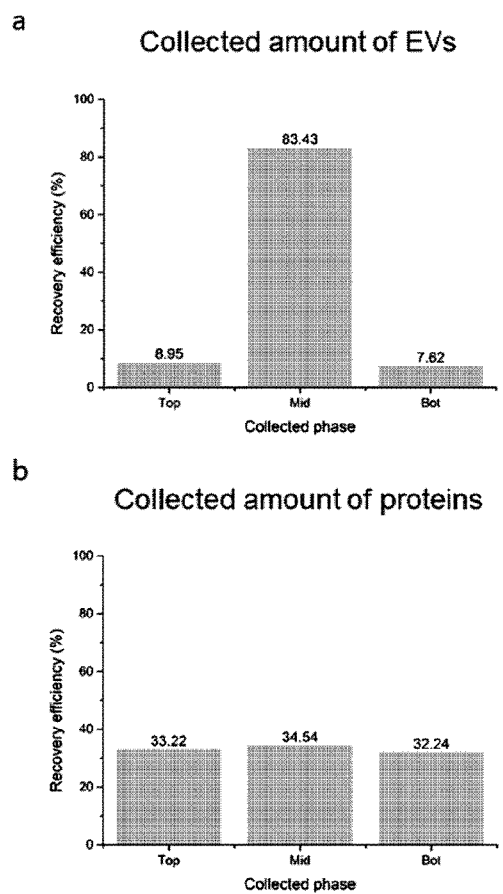
FIG. 7 is a series of graphs showing the recovery of exosomes (a) and BSA (b) isolated from each phase using a three-channel aqueous two-phase microfluidic chip according to an embodiment of the present invention.

In case that two phase aqueous microfluidic channel is used, the yield of the exosome was 83.43% as shown in FIG. 7a, and the removal rate of BSA was 65.46% which is similar to that of the single phase system as shown in FIG. 7b. This proves that the aqueous two phase microfluidic system of the present invention is very efficient for the isolation of exosomes. In particular, considering the efficacy of conventional methods of isolating exosomes using the ultracentrifugation is only 5~20%, the result of the present invention is very remarkable.

Experimental Example 2: Isolation of Exosomes in Plasma

The present inventors investigated whether the efficient isolation of the exosomes shown in Experimental Example 1 is reproduced in the plasma, which is a heterogeneous sample.

Figure 8:
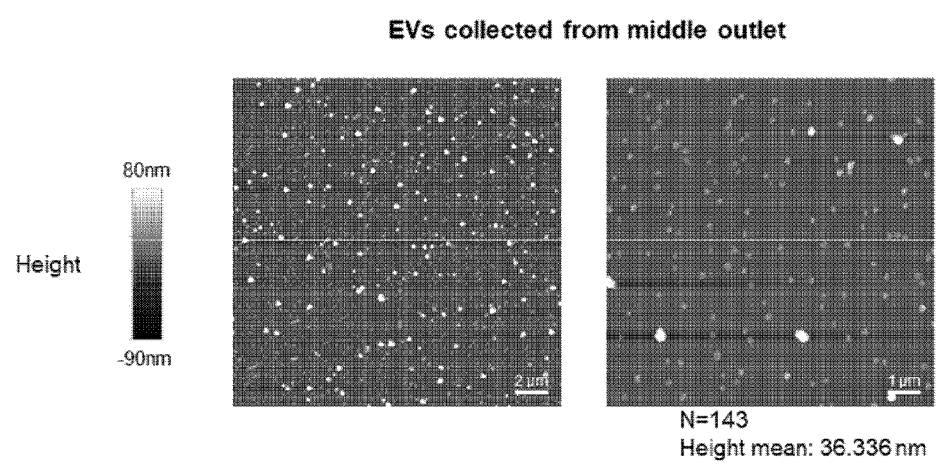
FIG. 8 is a series of atomic force microscopic images of plasma-derived exosomes isolated using a three-channel aqueous two-phase microfluidic chip according to an embodiment of the present invention.

To this end, specifically, after loading 400 μl of plasma sample onto the three-channel microfluidic channel prepared by Example 1 and forming a microfluid in the same manner as in Experiment Example 1. After the microfluidic isolation, microscopic images of a sample obtained from the intermediate channel was taken by an atomic force microscope (AFM). As a result, as shown in FIG. 8, it was confirmed that the exosomes were normally isolated from the plasma.

Figure 9:
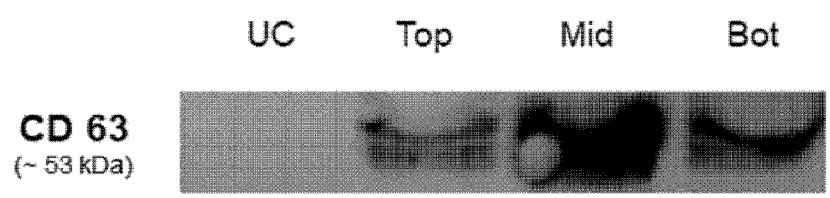
FIG. 9 is a photograph showing the result of detecting the plasma-derived exosomes isolated from each channel by using a 3-channel aqueous two-phase microfluidic chip in accordance with an embodiment of the present invention by western blot analysis using an anti-CD63 antibody.

In addition, the present inventors performed a 1% polyacrylamide gel electrophoresis (PAGE) of the sample obtained in the three channels in order to confirm the efficiency of the method for separating exosomes using the three-channel aqueous two phase microfluidic channel of the present invention. The PAGE gel was transferred onto a nylon membrane and western blot analysis was performed using an antibody specific to exosome marker CD63 (Abcam, MA, USA) (FIG. 9). As a control, a sample separated through ultracentrifugation was used. As a result, as shown in FIG. 9, the exosomes isolated by ultracentrifugation were too low in concentration so that the bands were almost invisible, whereas exosomes isolated using the 3-channel aqueous two phase microfluidic channel of the present invention were clearly detected. A very strong signal was observed in the intermediate channel. Although bands were observed in the upper and lower channels, the relative amount was found to be very small compared to the intermediate channel. This is a result of demonstrating that the three-channel aqueous two phase microfluidic channel of the present invention operates efficiently even when plasma is used as a sample.

As demonstrated through the experimental example described above, the method for isolating extracellular vesicles using an aqueous single-phase or aqueous two-phase microfluidic channel according to an embodiment of the present invention may be used for isolating small amount of extracellular vesicles produced in vivo and secreted to plasma as well as ones prepared in vitro through cell culture efficiently and thus may be used for the production of nanoparticle therapeutics and diagnosis of various diseases.

While the present invention has been particularly shown and described with reference to examples described above, it is to be understood that the invention is not limited to the disclosed examples, but, on the contrary, is intended to cover various modifications and equivalent arrangements included within the spirit and scope of the following claims. Accordingly, the true scope of the present invention should be determined by the technical idea of the following claims.

The invention claimed is:

1. A method for isolating extracellular vesicles from a sample containing the extracellular vesicles and proteins, said method comprising sequentially:
   preparing a microfluidic chip in which a microfluidic channel whose length is 18 to 30 cm is formed and (i) three inlets comprising an upper inlet, an intermediate inlet and a lower inlet and (ii) three outlets comprising an upper outlet connected to the upper inlet, an intermediate outlet connected to the intermediate inlet, and a lower outlet connected to the lower inlet are formed at both ends of the channel, respectively;
   injecting a first aqueous solution into the upper inlet and the lower inlet of the microfluidic chip to form a first microfluid and a second aqueous solution into the intermediate inlet of the microfluidic chip to form a second microfluid;
   injecting a sample containing extracellular vesicles and proteins into the intermediate inlet of the microfluidic chip; and
   recovering the second microfluid containing extracellular vesicles from the intermediate outlet,
   wherein the first aqueous solution is an aqueous solution in which at least one first solute selected from the group consisting of polyethylene glycol, polyvinylpyrrolidone, and polyvinyl alcohol is dissolved in water, and the second aqueous solution is an aqueous solution in which at least one second solute selected from the group consisting of ethylene oxide propylene oxide (EOPO), dextran, levan, poly(vinyl methyl ethyl ether), ammonium sulfate, sodium sulfate, magnesium sulfate, potassium phosphate and sodium carbonate is dissolved in water,
   wherein the first microfluid and the second microfluid are not mixed with each other due to their poor compatibility with each other, and thus the first microfluid forms an upper phase and a lower phase and the second microfluid forms an intermediate phase in the microfluidic channel, and
   wherein the sample flows in the intermediate phase and the proteins are diffused to the upper phase and the lower phase but the diffusion of extracellular vesicles to the upper phase and the lower phase is minimized.

2. The method of claim 1, wherein the concentration of the first solute is 1 to 5 wt %.

3. The method of claim 1, wherein the concentration of the second solute is 1 to 2 wt %.

4. The method of claim 1, wherein the sample is cell culture media, sweat, tear, urine, serum, or plasma.

5. The method of claim 1, wherein the extracellular vesicles are exosomes or microvesicles.

* * * * *